(12) United States Patent
Yoon

(10) Patent No.: US 11,596,778 B2
(45) Date of Patent: Mar. 7, 2023

(54) INSERTION TYPE DRUG INJECTION DEVICE

(71) Applicant: HUONS MEDICAL CO., LTD., Seongnam-si (KR)

(72) Inventor: Sung Tae Yoon, Seongnam-si (KR)

(73) Assignee: HUONS MEDICAL CO., LTD., Seongnam-si (KR)

( * ) Notice: Subject to any disclaimer, the term of this patent is extended or adjusted under 35 U.S.C. 154(b) by 101 days.

(21) Appl. No.: 17/052,846

(22) PCT Filed: Apr. 23, 2020

(86) PCT No.: PCT/KR2020/005369
§ 371 (c)(1),
(2) Date: Nov. 4, 2020

(87) PCT Pub. No.: WO2020/222462
PCT Pub. Date: Nov. 5, 2020

(65) Prior Publication Data
US 2021/0213261 A1    Jul. 15, 2021

(30) Foreign Application Priority Data

Apr. 30, 2019 (KR) .................. 10-2019-0051023
Dec. 13, 2019 (KR) .................. 10-2019-0167117

(51) Int. Cl.
*A61M 31/00* (2006.01)
*A61M 5/46* (2006.01)
(Continued)

(52) U.S. Cl.
CPC ............ *A61M 31/00* (2013.01); *A61M 5/158* (2013.01); *A61M 5/46* (2013.01); *A61M 5/3295* (2013.01);
(Continued)

(58) Field of Classification Search
CPC ........ A61M 31/00; A61M 5/158; A61M 5/46; A61M 2205/3592; A61M 2210/1475;
(Continued)

(56) References Cited

U.S. PATENT DOCUMENTS 6,743,211 B1 * 6/2004 Prausnitz ......... A61B 5/150083
604/173
10,434,239 B1 * 10/2019 Briggs ................ A61M 1/3681
(Continued)

FOREIGN PATENT DOCUMENTS

JP    2015198910 A    11/2015
KR    101154134 B1    6/2012
(Continued)

*Primary Examiner* — Katherine H Schwiker
*Assistant Examiner* — Phoebe Anne Staton
(74) *Attorney, Agent, or Firm* — Rabin & Berdo, P.C.

(57) ABSTRACT

The present disclosure relates to an insertion type drug injection device capable of being inserted into a body for injecting a drug into a skin, including: a main body having an open insert part and formed in a tubular shape having a hollow space therein, a needle assembly formed in the insert part, provided with a plurality of needles, and including a pneumatic port and a drug injection port, and a drug injection pipe inserted into the main body and connected to a drug injection port of the needle assembly, and an air flowing pipe connected to the pneumatic port.

16 Claims, 6 Drawing Sheets

(51) Int. Cl.
*A61M 5/158* (2006.01)
*A61M 5/32* (2006.01)
*A61M 25/00* (2006.01)

(52) U.S. Cl.
CPC . *A61M 25/0084* (2013.01); *A61M 2205/3592* (2013.01); *A61M 2210/1475* (2013.01)

(58) Field of Classification Search
CPC ............ A61M 25/0084; A61M 5/3295; A61M 2025/0085; A61M 5/162; A61M 5/32; A61M 5/3298; A61M 2005/1581; A61M 2005/1588; A61M 2205/584; A61M 5/5086; A61F 13/42; A61F 2250/0097; G06Q 30/018
See application file for complete search history.

(56) References Cited

U.S. PATENT DOCUMENTS

| | | | |
|---|---|---|---|
| 2008/0033337 | A1* | 2/2008 | Dougherty .............. A61F 13/28 604/11 |
| 2011/0270184 | A1 | 11/2011 | Gunday et al. |
| 2014/0343481 | A1* | 11/2014 | Ignon .................. A61M 5/3298 604/21 |
| 2016/0175544 | A1* | 6/2016 | Koska ................ A61M 5/3216 604/117 |
| 2016/0263358 | A1* | 9/2016 | Unger .................... A61B 90/02 |
| 2018/0200495 | A1* | 7/2018 | Sumida .................... A61M 5/46 |
| 2019/0151674 | A1* | 5/2019 | Yoon ........................ A61N 1/06 |
| 2019/0159804 | A1* | 5/2019 | Cameron ............ A61M 5/3286 |

FOREIGN PATENT DOCUMENTS

| | | | | |
|---|---|---|---|---|
| KR | 101405292 | B1 | 6/2014 | |
| KR | 1020140079555 | A | 6/2014 | |
| KR | 1020180108169 | A | 10/2018 | |
| KR | 101963601 | B1 | 4/2019 | |
| KR | 101738675 | B1 * | 5/2022 | ............. A61M 5/46 |

\* cited by examiner

INSERTION TYPE DRUG INJECTION DEVICE

TECHNICAL FIELD

The present disclosure relates to an insertion type drug injection device, and more specifically, to an insertion type drug injection device capable of injecting an appropriate amount into the skin at an accurate depth regardless of the operator's skill level.

BACKGROUND ART

In general, an insertion type drug injection device is a device that injects a drug into the body. As an example, there is a filler procedure using an insertion type drug injection device, which is a procedure in which a substance called filler is injected into the skin. The scope of application of the filler procedure is expanding, and the filler procedure is performed for vaginal plastic surgery, colpoxerosis, and other intravaginal drug injection. However, the drug injection procedure is performed in a way that the operator injects the drug into the inner wall of the vagina one by one using a disposable syringe filled with drug, so the depth of the injection and the dose of the injected drug may be affected by the operator's skill level. Since it is difficult for the operator to check the injection site, it may be a burden on the operator during the procedure, and there is a problem that the patient feels uncomfortable during the procedure. In addition, since the injection needle is exposed, there is a problem of causing pain by hurting the inner wall of the vagina in the process of moving to injection site during the procedure.

SUMMARY

Technical Problem

The present disclosure has been made in order to solve the problems of the prior art, and an object of the present disclosure is to provide an insertion type drug injection device, with which it is possible to inject drug without damaging the skin inside the body, and a practitioner is able to easily check the depth of the injection with the naked eye, and perform safe and rapid procedure while minimizing pain.

Technical Solution

An object of the present disclosure as described above is to provide an insertion type drug injection device capable of being inserted into a body for injecting a drug into a skin, which may include a main body having an open insert part at a head thereof and formed in a tubular shape having a hollow space therein, a needle assembly formed in the insert part, provided with a plurality of needles, and including a pneumatic port and a drug injection port, and a drug injection pipe inserted into the main body and connected to a drug injection port of the needle assembly, and an air flowing pipe connected to the pneumatic port.

The needle assembly may include a holder unit formed in the insert part, and including a plurality of needle holders including needle holes for needles to be penetrated therethrough, and a pneumatic port having a suction hole; and an injection member coupled to the holder unit, and including a plurality of needles formed thereon, and a flow path for injecting the drug into the plurality of needles.

The holder unit may further include a holder unit body with openings formed at top and bottom portions, a panel formed horizontally inside the holder unit body and having the needle holder formed thereon, and a guide formed around the bottom opening of the holder unit body and being brought into contact with the skin.

The guide may be formed to protrude further than the insert part of the main body.

The injection member may include a drug injection port communicating with the flow path, and may be formed to allow the flow path to communicate with the plurality of needles.

The injection member may include: an upper body coupled to the holder unit, and including the flow path for injecting the drug, a drug injection port communicating with the flow path, and the plurality of needles communicating with the flow path; and a lower body coupled to the upper body, and including the needle holders for the plurality of needles to be penetrated through.

The holder unit may be formed integrally with the insert part of the main body, or detachably coupled to the insert part of the main body.

The main body may include an air discharge pipe coupling part connected to the air flowing pipe inside the main body, and an air discharge pipe may be connected to the air discharge pipe coupling part.

The main body may include a checking means that enables checking of one or more of insertion depth and rotation angle.

The main body may include a genuineness identification unit including a short-range wireless communication unit to determine a genuineness of a product by communicating with an external control unit.

Advantageous Effects

According to the present disclosure, there is an effect that a filler procedure can be performed without hurting the skin inside a body, and a safe and rapid procedure can be performed without causing pain.

In addition, when assembling a main body, UV bonding is performed on the portions to be connected, but with the reduced bonding volume, so that the assembly process can be improved.

In addition, the insertion depth and the angle of rotation into the injection site can be checked through the checking means, so that the procedure can be safely and conveniently performed.

In addition, by the indication panel that changes colors after use, it is possible to prevent reuse of the product used once, thereby ensuring safety.

Further, during the procedure, since the procedure can be performed by determining genuineness of the drug injection device, there is an effect of increased reliability of the procedure.

BEST MODE

An insertion type drug injection device according to the present disclosure is an insertion type drug injection device capable of being inserted into a body for injecting a drug into a skin and includes a main body having an open insert part at a head thereof and formed in a tubular shape having a hollow space therein, a needle assembly formed in the insert part, provided with a plurality of needles, and including a pneumatic port and a drug injection port, and a drug injection pipe inserted into the main body and connected to a drug injection port of the needle assembly, and an air flowing pipe connected to the pneumatic port.

DETAILED DESCRIPTION

Hereinafter, preferred embodiments of the present disclosure will be described in detail with reference to the accompanying drawings.

The terms to be described below are defined in consideration of functions in the present disclosure, and it is noted that they should be interpreted as a concept consistent with the technical idea of the present disclosure and a meaning commonly or generally recognized in the art. Further, in the following description of the present disclosure, a detailed description of known functions and configurations incorporated herein will be omitted when it may make the subject matter of the present disclosure rather unclear. Here, the accompanying drawings are partially exaggerated or simplified for convenience and clarity of explanation and understanding of the configuration and operation of the technology, and each component does not exactly match the actual size. It should be noted that, while the embodiments are described herein with reference to the example of application to a body, in particular, to the vagina of a woman, the present disclosure is not necessarily limited thereto and can be used for various body procedures. It should be noted that, while the embodiments are described herein with reference to the example of application to a body, in particular, to the vagina of a woman, the present disclosure is not necessarily limited thereto and can be used for various body procedures.

Figure 1:
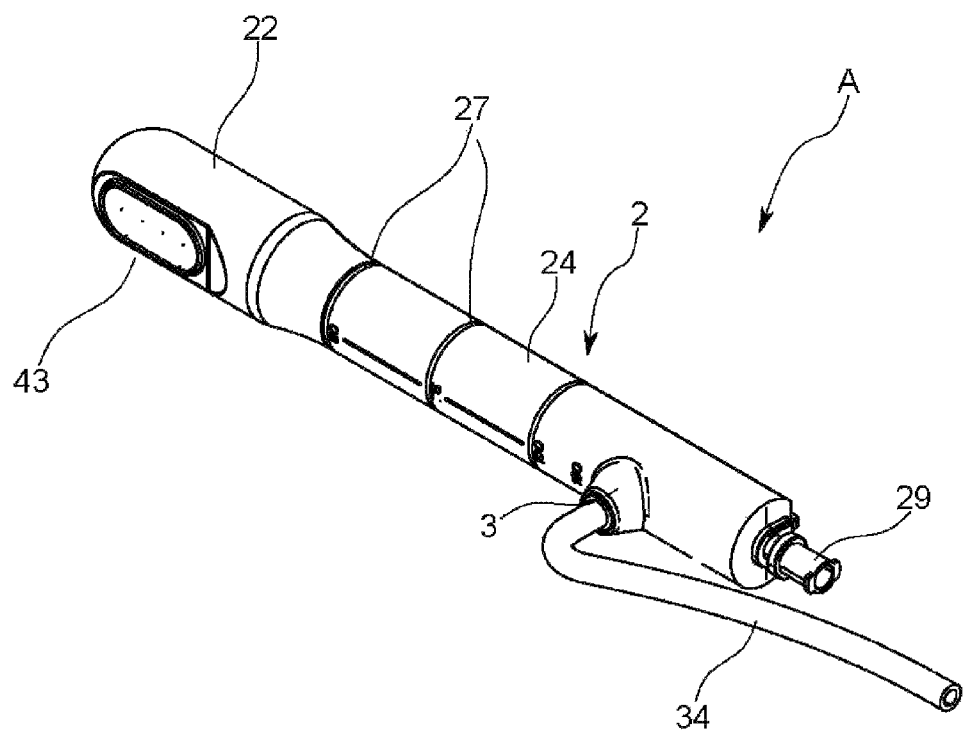
FIG. 1 is a perspective view showing an insertion type drug injection device according to the present disclosure.
Figure 2:
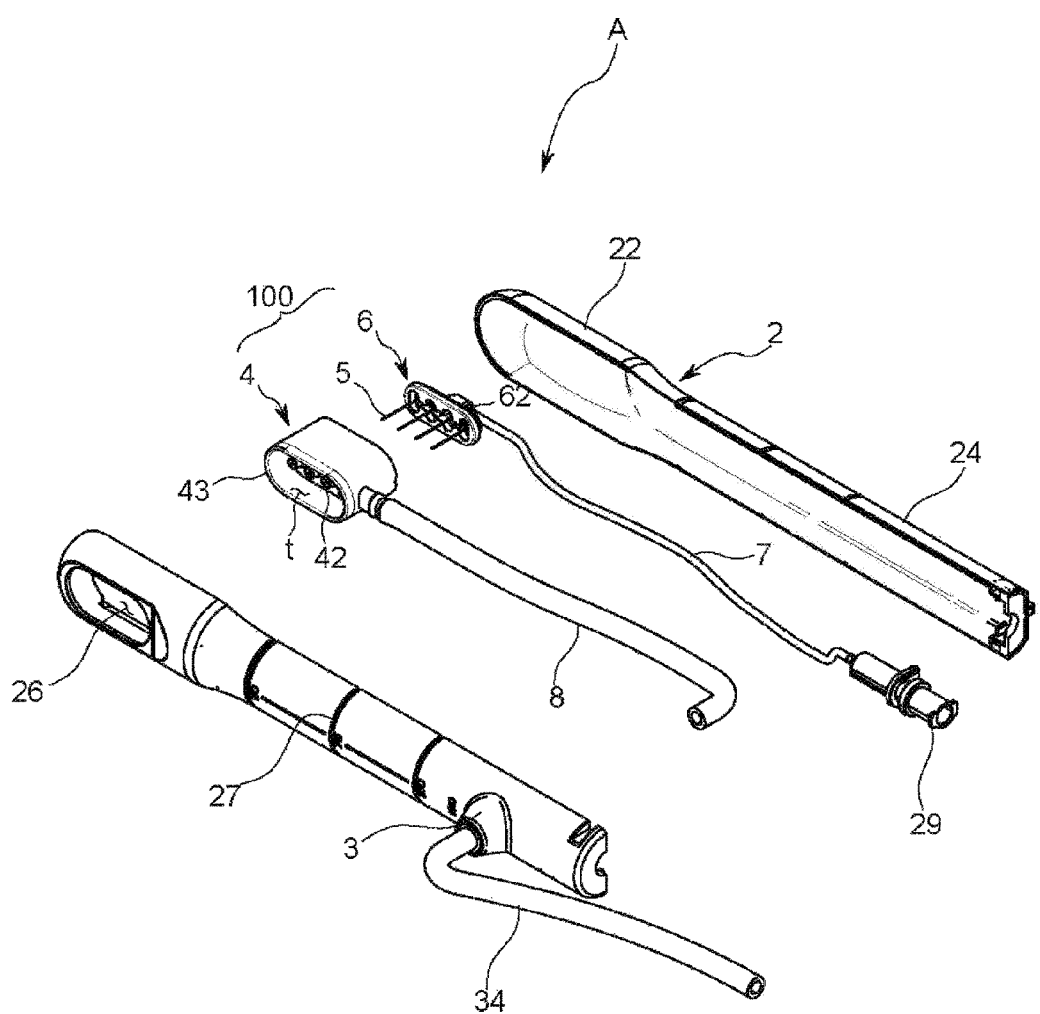
FIG. 2 is an exploded perspective view showing the insertion type drug injection device according to the present disclosure.
Figure 3:
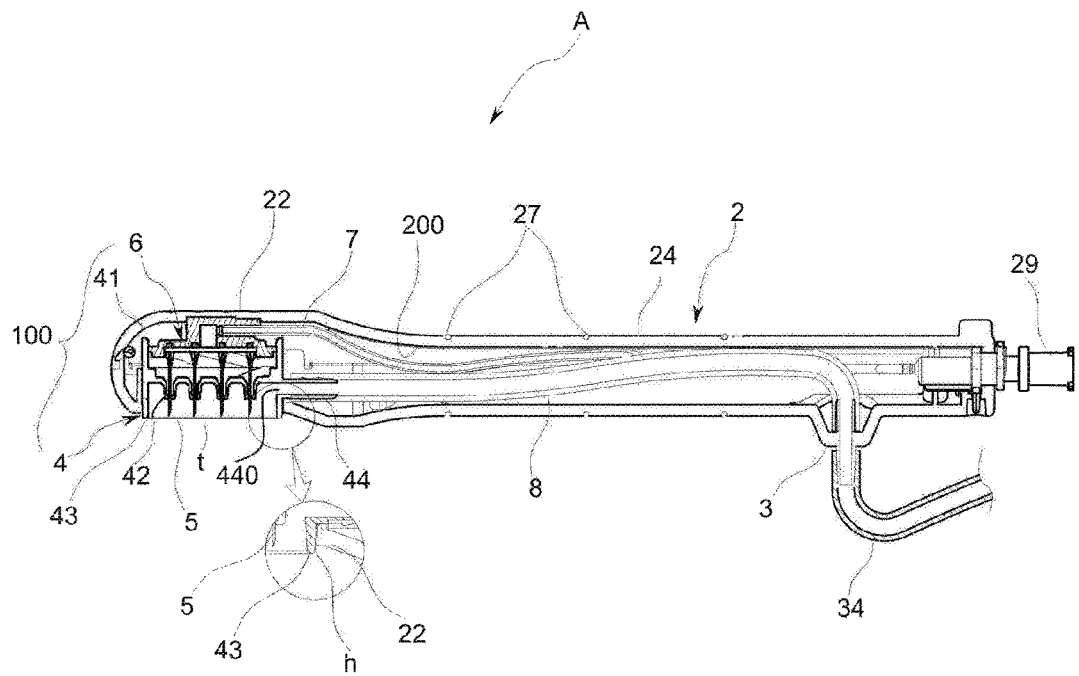
FIG. 3 is a cross-sectional view showing the insertion type drug injection device according to the present disclosure.
Figure 4:
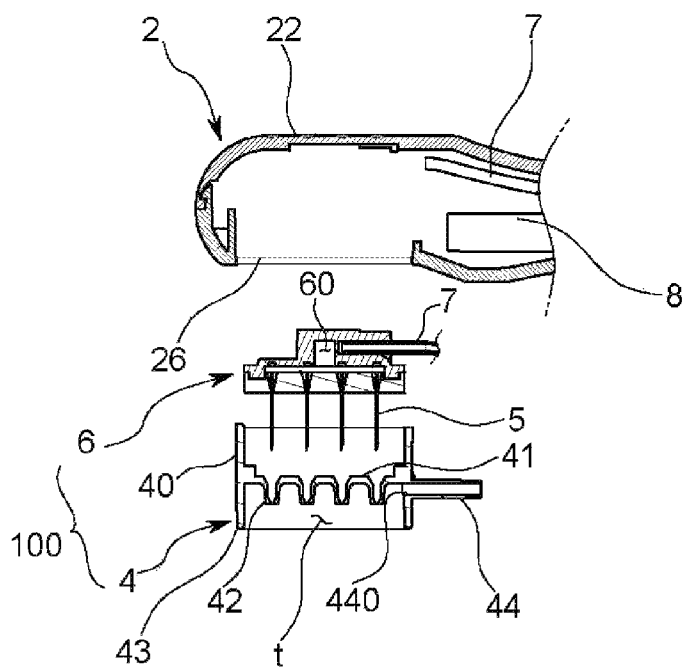
FIG. 4 is an exploded cross-sectional view showing the insertion type drug injection device according to the present disclosure.
Figure 5:
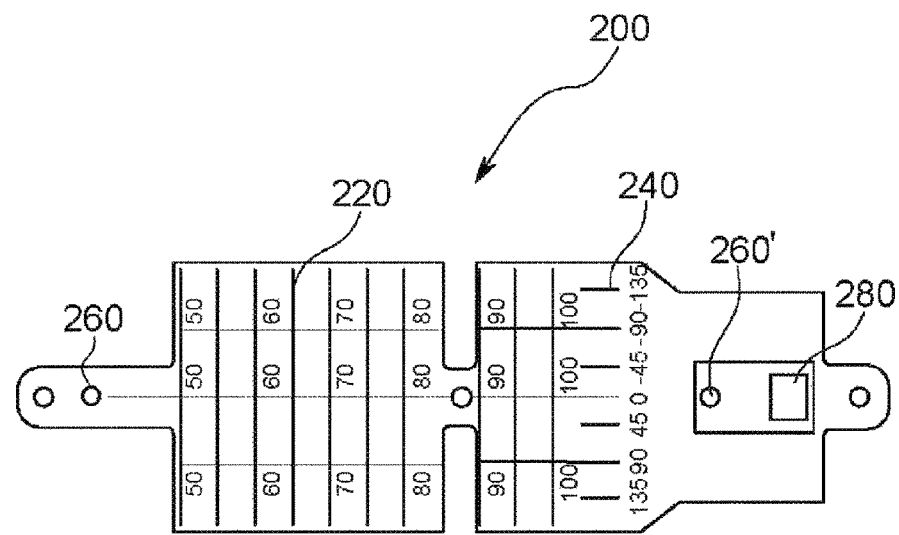
FIG. 5 is a plan view showing an "indication panel" of the insertion type drug injection device according to the present disclosure.
Figure 6:
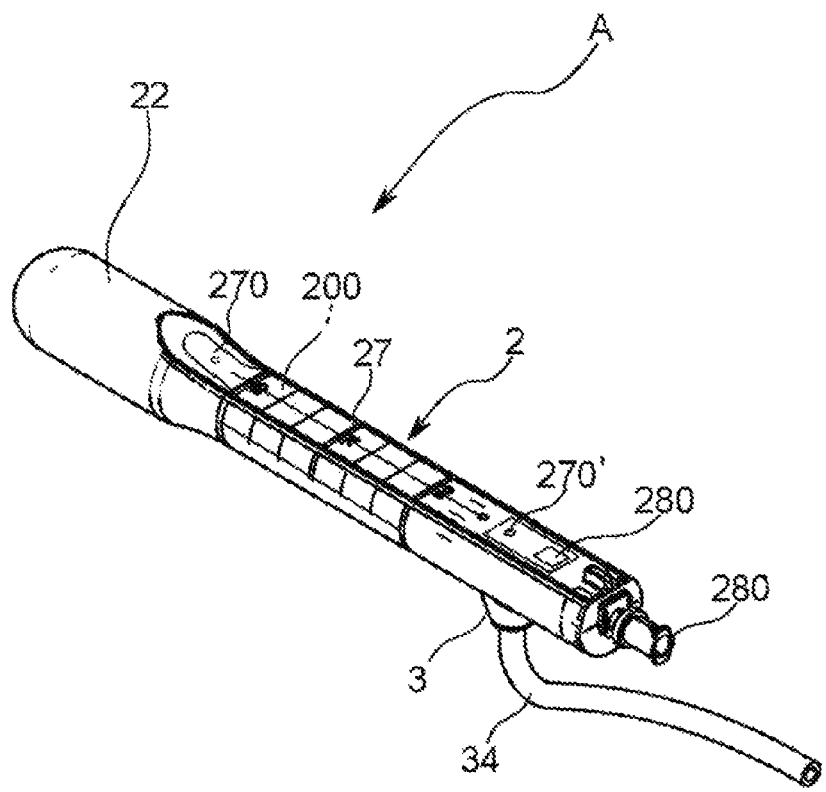
FIG. 6 is a perspective view showing a "color changing part" of the insertion type drug injection device according to the present disclosure.
Figure 7:
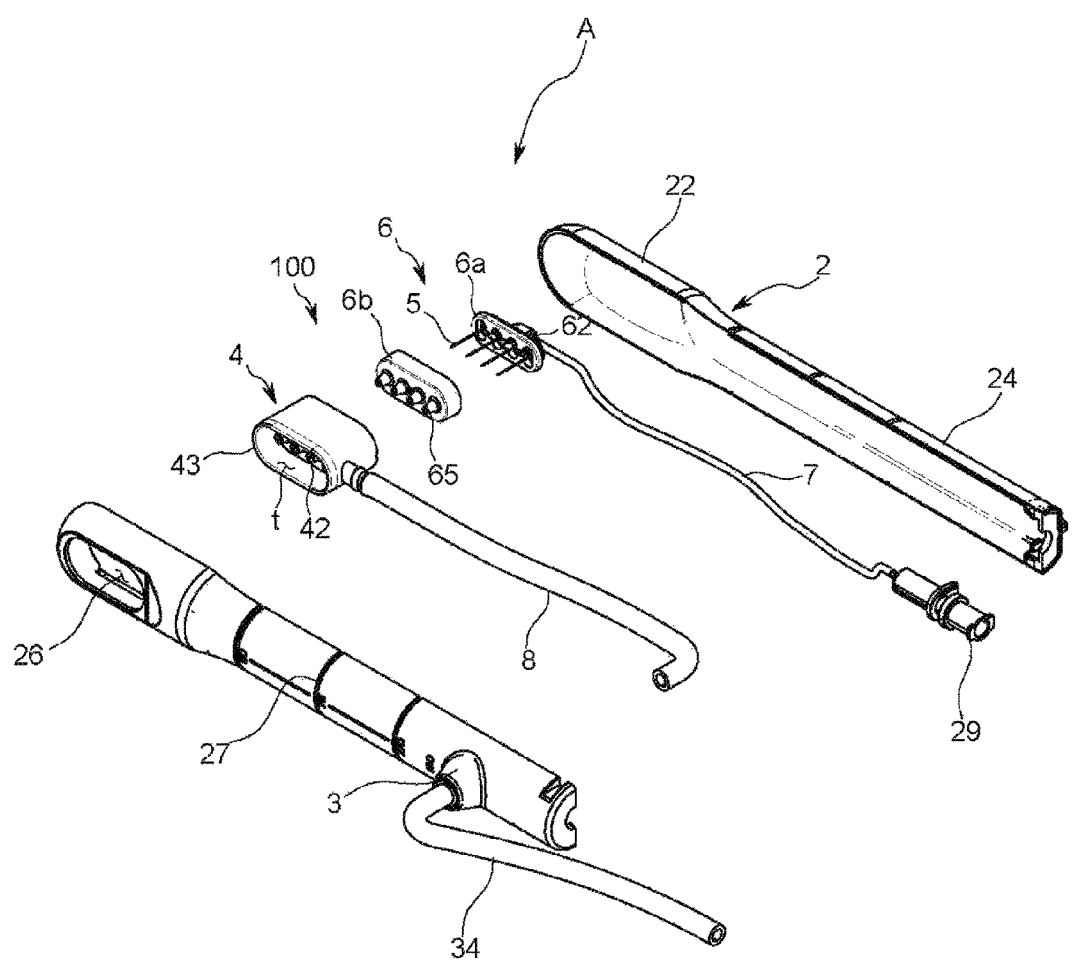
FIG. 7 is an exploded perspective view showing an insertion type drug injection device according to another embodiment.
Figure 8:
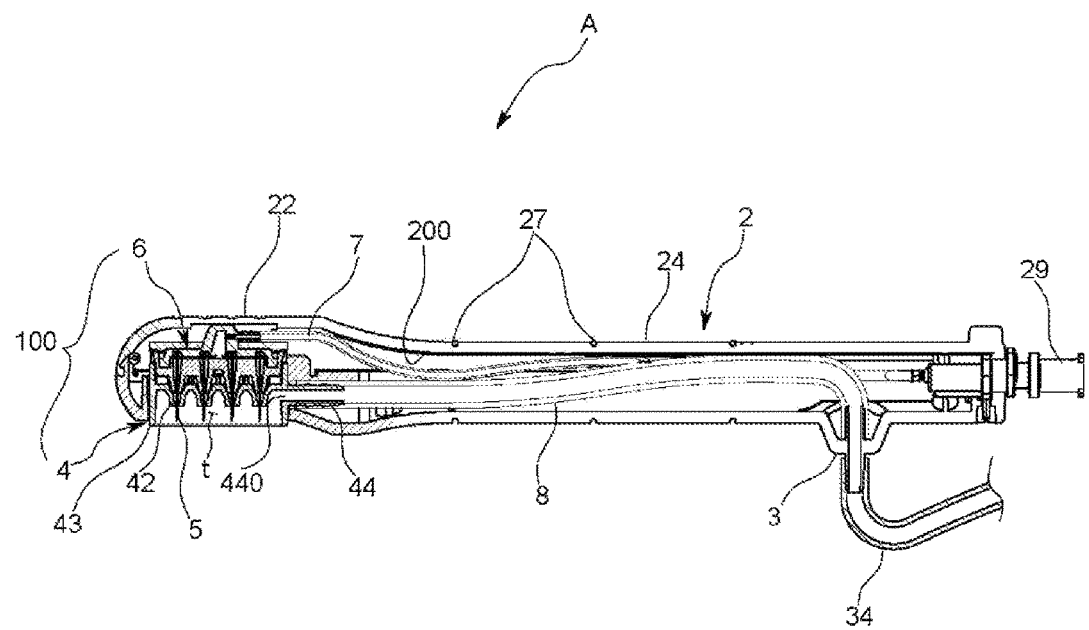
FIG. 8 is a cross-sectional view showing the insertion type drug injection device according to another embodiment.
Figure 9:
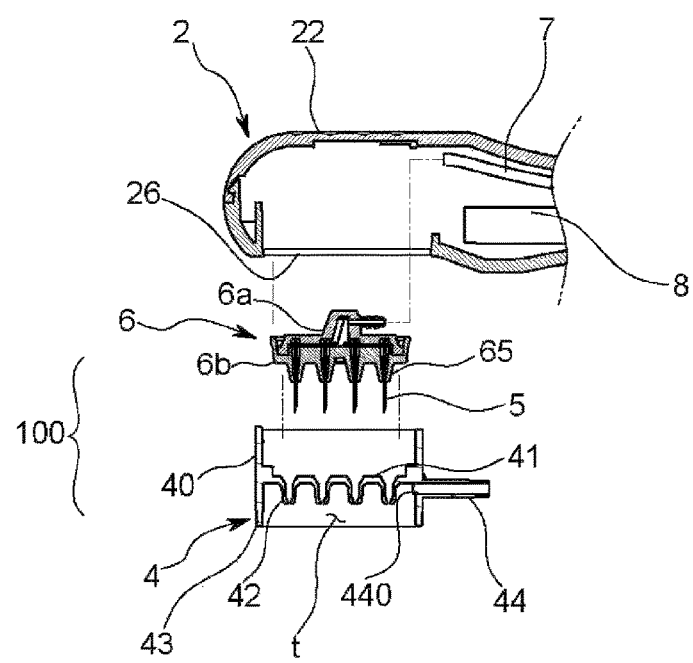
FIG. 9 is an exploded cross-sectional view showing the insertion type drug injection device according to another embodiment.

In the accompanying drawings, FIG. 1 is a perspective view showing an insertion type drug injection device according to the present disclosure. FIG. 2 is an exploded perspective view showing the insertion type drug injection device according to the present disclosure. FIG. 3 is a cross-sectional view showing the insertion type drug injection device according to the present disclosure. FIG. 4 is an exploded cross-sectional view showing the insertion type drug injection device according to the present disclosure. FIG. 5 is a plan view showing an "indication panel" of the insertion type drug injection device according to the present disclosure, FIG. 6 is a perspective view showing a "color changing part" of the insertion type drug injection device according to the present disclosure. FIG. 7 is an exploded perspective view showing an insertion type drug injection device according to another embodiment. FIG. 8 is a cross-sectional view showing the insertion type drug injection device according to another embodiment. FIG. 9 is an exploded cross-sectional view showing the insertion type drug injection device according to another embodiment.

As shown in FIGS. 1 to 6, the insertion type drug injection device according to the present disclosure includes a main body 2, a needle assembly 100, a drug injection pipe 7, an air flowing pipe 8, an air discharge pipe 34, a color changing part 260, and a genuineness identification unit 280.

The main body 2 includes a head 22 on which an insert part 26 open to communicate with the outside is formed, and a body 24 connected to the head 22 and formed in a tubular shape including a hollow space therein.

The main body 2 is formed such that the tubular body 24 has a predetermined length, the head 22 is formed at the end of the body 24, and the head 22 may be formed in a curved surface to facilitate insertion into the vagina. The insert part 26 is formed as a flat cutoff part formed on one side of the head 22 and is open in an elliptical shape. Preferably, the main body 2 is made of a material having high transparency, harmless to the human body, and having strong strength, and may be made of a resin such as transparent polycarbonate (PC), polymethyl methacrylate (PMMA), polystyrene (PS), polypropylene (PP), and polyethylene (PE). Most preferably, a polycarbonate material may be used.

The main body 2 includes an air discharge pipe coupling part 3 formed on an outer surface and connected to the air flowing pipe 8 formed inside, and the air discharge pipe 34 is connected to the air discharge pipe coupling part 3.

The needle assembly 100 includes a holder unit 4 and an injection member 6. The holder unit 4 may be inserted into and coupled to the head 22 of the main body 2, or may be integrated with the head 22 by molding. The holder unit 4 includes a plurality of needle holders 65 having needle holes, and also includes, formed on one side, a pneumatic port 44 having a suction hole 440. Preferably, the holder unit 4 may be made of a polypropylene or polyethylene material that is harmless to the human body.

The holder unit 4 includes a holder unit body 40 having openings on top and bottom sides respectively, and a panel 41 formed horizontally inside the holder unit body 40, and there are a plurality of needle holders 65 formed on the panel 41. Each needle holder 65 includes a needle hole for the needle 5 to penetrate therethrough.

In addition, a guide 43 is formed around the bottom opening of the holder unit body 40, and the guide 43 is brought into contact with the skin. Preferably, the guide 43 is formed to protrude further than the insert part 26 of the head 22.

The drug injection pipe 7 is inserted into the main body 2 and connected to a drug injection port 62 of the needle assembly 100.

The air flowing pipe 8 is connected to the pneumatic port 44 to generate a suction pressure.

Meanwhile, as shown in FIGS. 7 to 9, according to another embodiment, the needle assembly 100 includes the holder unit 4 and the injection member 6, and the holder unit 4 includes a plurality of needle holder fitting holes 42 having needle holes, and also includes, on one side thereof, the pneumatic port 44 having the suction hole 440.

The needle holder fitting holes 42 are formed to be concave to allow fitting of the needle holder 65 to be described below therein, and includes the needle holes for the needle 5 to penetrate therethrough.

The injection member 6 includes an upper body 6a including a flow path 60 coupled to the holder unit 4 to inject a drug, the drug injection port 62 communicating with the flow path 60, and the plurality of needles 5 penetrating the needle holders 65 communicating with the flow path 60; and a lower body 6b coupled to the upper body 6a and including the needle holders 65 through which the plurality of needles 5 are penetrated. The needle holders 65 are fitted in the needle holder fitting holes 42 to have a sealing force, and include the needle holes for the needles 5 to be penetrated therethrough.

A plurality of needles 5 may be provided, and numbers and arrangements of the needles may be such that an arrangement in a row, or an arrangement in a staggered fashion, or an arrangement in a plurality of rows in parallel may be used, although it is clear that various modifications of the numbers and arrangements of the needles are possible.

The plurality of needles 5 are positioned inward from the insert part 26 of the head 22 by 0.1 to 2.5 mm, so that the needles 5 are not exposed with reference to the insert part 26. The needle 5 is formed with a length of 1.5 to 5.5 mm so as to be inserted at least 1.5 mm and up to 5.5 mm into the skin of the injection site.

Meanwhile, the guide 43 may be additionally formed at the bottom opening of the holder unit 4, and the guide 43 is formed to protrude further than the insert part 26 of the head 22. The guide 43 is formed to protrude further than the insert part 26 of the head 22 by 0.1 to 2.5 mm.

The needles are positioned to be received in the guide 43, and formed with the length of 1.5 to 5.5 mm. When the length of the exposed syringe is less than 1.5 mm, there is a concern that the effect of the procedure may be degraded when considering the skin thickness of the injection site, and when it exceeds 5.5 mm, there is a concern that the effect of the procedure may be degraded when considering excessive pain and skin thickness at the injection site. More preferably, the length of the needle 5 is set to 2.0 to 3.0 mm.

In addition, the guide 43 is formed around the bottom opening, and the guide 43 is formed to protrude further than the insert part 26 of the head 22. Meanwhile, the guide 43 is preferably formed with a height h so as to protrude further than the insert part 26 of the head 22 by 0.5 to 2.5 mm. As the guide 43 presses the skin at the injection site, the skin is bulged into the guide 43, or, when vacuum is formed inside the guide 43 by an additional suction action, the skin is more strongly introduced into the guide 43, and the needle 5 is inserted into the skin. Meanwhile, when the protruding length of the guide 43 is less than 0.5 mm, while moving to the injection site, there is a concern that a scratch injury on the skin due to the needle 5 may occur when the skin is even slightly introduced into the guide 43. Meanwhile, when the guide 43 is formed to protrude by more than 2.5 mm, since a strong suction pressure need to be formed in order to cause the needles 5 to be inserted into the skin, there is a concern that pain is caused. More preferably, the guide 43 is formed to protrude further than the insert part 26 of the head 22 by 0.7~1.2 mm. The guide 43 formed to protrude as described above can be brought into contact with the skin before the head 22, and when pressed, can cause the skin to be constrained in a lower space t of the holder unit body 40 so that it may maintain a state in which air inflow is blocked, thereby providing airtightness.

The holder unit 4 is manufactured as an integral type, i.e., integrally formed with the head 22 of the main body 2. Alternatively, the holder unit 4 may be formed as a detachable type that can be fitted to the head 22 of the main body 2 and detached therefrom. Therefore, the holder unit 4 may be integrally formed with the insert part 26 of the head 22 of the main body 2 or may be mounted by being fitted in the insert part 26.

Meanwhile, the air flowing pipe 8 is inserted into the main body 2 and connected, at one end, to the pneumatic port 44 of the holder unit 4. The pneumatic port 44 is formed lower than the panel 41, that is, formed closer to the guide 43, so that the lower space t, which is one of internal spaces of the holder unit body 40 partitioned by the panel 41, is communicated with the pneumatic port 44. Positive pressure and negative pressure may be sequentially formed with the air flowing pipe 8. For example, the negative pressure may be formed in the process of inserting the needle into the injection site, and the positive pressure may be applied to release the vacuum after drug injection.

The other end of the air flowing pipe 8 is connected to an air flowing pipe coupling part 3 provided in the main body 2. The air flowing pipe coupling part 3 includes an out port protruding to the outside of the main body 2 and an in port oriented toward the inside of the main body 2, and the other end of the air flowing pipe 8 is connected to the in port, and the air discharge pipe 34 is connected to the out port.

Meanwhile, the injection member 6 includes the plurality of needles 5 coupled to the holder unit 4 and penetrating the needle holders 65, the flow path 60 for injecting a drug into the plurality of needles 5, the drug injection port 62 communicating with the flow path, and the plurality of needles 5 communicated with the flow path 60.

One end of the drug injection pipe 7 provided inside the main body 2 is connected to the drug injection port 62, and the other end of the drug injection pipe 7 is connected to a syringe connector 29 formed at the end of the main body 2. Therefore, a syringe (not shown) is connected to the syringe connector 29 so that the drug can be continuously supplied.

Meanwhile, the body 24 of the main body 2 is provided with a checking means for checking one or more of insertion depth and rotation angle. The checking means may be one or more selected from the group consisting of a scale, a partition line, numbers, symbols, letters, prints, stickers, colors, protrusions, and indication panels. For example, a plurality of partition lines 27 may be formed on the body 24 at regular intervals. According to the degree of insertion of the plurality of partition lines 27 into the injection site, an insertion depth may be calculated according to the interval and number of the partition lines 27. Alternatively, the checking means may include a means that enables checking with the naked eye, such as scales or consecutive numbers, letters, colors, and the like, and thus the insertion depth may be checked with the naked eye. However, the checking means is not limited to those listed above and should be interpreted as including any means that can visually determine the degree of insertion.

The body 24 of the main body 2 is provided with the plurality of partition lines 27 for checking the insertion depth. The partition lines 27 may be formed by indenting an outer peripheral surface of the body 24 by a predetermined depth in the circumferential direction or may have a shape protruding in the circumferential direction. In addition, the indication panel 200 is formed inside the body of the main body 2, on which insertion depth scales 220 for checking the insertion depth are indicated. Angle measurement scales 240 may be further formed on the indication panel 200 so as to measure the insertion rotation angle. The insertion depth scales 220 or the angle measurement scales 240 are formed of text or color to improve visibility. In addition, the insertion depth scales 220 or the angle measurement scales 240 may be formed by medical silicone ink or UV printing, but not limited thereto.

As an example of the checking means, as shown in FIGS. 1 and 2, three lines of partition lines 27 are formed, and the partition lines 27 are arranged at 1 to 3 cm intervals. It goes without saying that this is merely an example, and the spacing between the partition lines 27 may be variously modified.

Meanwhile, the checking means may include a color changing part that changes color when reacting with the liquid. The color changing part 260 may be a discoloration test paper, so that the color before use and the color after use are different, and in the process of use, the color changes to a different color after contact with the body fluids of the human body. For example, the body 24 of the main body 2 includes a through hole 270 formed therein, and the indication panel 200 includes the color changing part 260 that is formed to correspond to the through hole 270 and that changes colors when reacting with a liquid. By making it possible to know whether the color changing part 260 has been used by visually checking whether it is discolored, reuse may be prevented. Further, in addition to checking possible reuse, a color changing part 260' may be additionally included on the inner surface of the main body 2 of the insertion type drug injection device in order to prevent the used insertion type drug injection device from being reused after disinfection. More preferably, the color changing part 260' may be additionally included on the inner surface of the indication panel 200 of the main body 2, so that whether the drug injection device is cleaned or disinfected can be visually checked. Meanwhile, a through hole corresponding to the color changing part 260' is formed such that upon inflow of a disinfectant or cleaning solution through the through hole, the color changing part 260' changes the color. This may prevent reuse after use.

Meanwhile, the main body may include a genuineness identification unit 280 having a short-range wireless communication unit in order to communicate with an external control unit (not shown) to determine whether the product is genuine. The short-range wireless communication unit includes near field communication (NFC) or radio-frequency identification (RFID). The genuineness identification unit 280 may be formed on the indication panel 200 as a checking means for the main body. By reading an ID assigned to each insertion type drug injection device A, the genuineness may be determined, and when a genuine insertion type drug injection device A is connected to the device, the control unit may recognize the genuineness of the product and operate the device to perform the procedure.

Hereinafter, the operation of the present disclosure will be described.

The insertion type drug injection device A according to the present disclosure is connected to a controller including a suction generating unit and a drug injection unit.

The end of the insertion type drug injection device according to the present disclosure is connected to a hose of the controller. To briefly describe the controller, the controller includes: a main board connected to a motor to provide an electrical signal so as to control drug injection of the needles 5; an air hose connected to the needle assembly; a first suction pipe provided in the controller and connected in communication with the air hose; an air filter provided in the controller and configured to filter air sucked from the air hose; a suction pressure sensor formed on the main board and configured to sense a suction pressure of the connector; a suction motor configured to generate the suction pressure so as to suck air from the air filter; a solenoid valve configured to control opening and closing; a microcomputer formed on the main board and configured to detect an insertion of the needle 5 into the skin by comparing the suction pressure transmitted from a suction pressure sensor with an injection amount, and control the amount of operation of a motor of an injector to set an amount of drug of a syringe to be injected through the needle 5; a power switch configured to control on and off of the injection device; and a power supply configured to supply power to the injection device.

The head 22 of the main body 2 of the insertion type drug injection device according to the present disclosure is inserted into the vagina to an appropriate depth with reference to the partition lines 27, and then adjusted such that the injection member 6 faces the injection site.

Then, the suction pressure is generated through the air flowing pipe 8, and the skin is sucked into the lower space t of the holder unit body 40 and the inside of the guide 43, such that the end of the needle 5 is inserted into the skin. The drug is then injected into the skin through the needles 5. Because the needles 5 are inserted in the skin while the drug is being injected, blood or other body fluids may come out, but this may be sucked into the pneumatic port 44, the air flowing pipe 8, and the air discharge pipe and discharged to the outside. When the drug injection is complete, the suction pressure is released, and the insertion type drug injection device A is moved to another injection site and repeats the drug injection procedure.

The present disclosure is not limited by the embodiments described above and the accompanying drawings, and various modifications and applications not illustrated within the scope not departing from the technical spirit of the present disclosure are possible, as well as substitution of components and change to other equivalent embodiments are possible, and accordingly, contents related to modifications and applications of the features of the present disclosure should be construed to be included in a scope of the present disclosure.

INDUSTRIAL APPLICABILITY

The present disclosure relates to an insertion type drug injection device, which is used for injecting a drug into a body.

What is claimed is:

1. An insertion type drug injection device insertable into a body for injecting a drug into a skin, the device comprising:
   a main body having an open insert part at a head thereof and formed in a tubular shape having a hollow space therein;
   a needle assembly formed in the insert part, provided with a plurality of needles, and including a pneumatic port and a drug injection port, the needle assembly including:
      a holder unit formed in the insert part, and including a plurality of needle holders including needle holes for the plurality of needles to be penetrated therethrough, and the pneumatic port having a suction hole; and an injection member coupled to the holder unit, and including the plurality of needles formed thereon, and a flow path for injecting the drug into the plurality of needles;
a drug injection pipe inserted into the main body and connected to the drug injection port of the needle assembly; and
an air flowing pipe connected to the pneumatic port of the needle assembly to generate a suction pressure,
wherein the holder unit includes a holder unit body with a lower space,
wherein each needle of the plurality of needles is entirely positioned inward of the insert part of the main body, and
wherein suction pressure is configured to be generated through the air flowing pipe such that the skin is sucked into the lower space of the holder unit body and such that the plurality of needles is inserted into the skin to thereby inject the drug into the skin.

2. The insertion type drug injection device according to claim 1, wherein the holder unit includes a panel formed horizontally inside the holder unit body and having a needle holder formed thereon, and wherein the lower space is partitioned by the panel.

3. The insertion type drug injection device according to claim 2, wherein the holder unit further includes a guide formed around a bottom opening of the holder unit body and configured to be brought into contact with the skin.

4. The insertion type drug injection device according to claim 3, wherein the guide is formed to protrude further than the insert part of the main body.

5. The insertion type drug injection device according to claim 3, wherein the guide is formed to protrude further than the insert part of the main body by 0.1 to 2.5 mm.

6. The insertion type drug injection device according to claim 3, wherein the plurality of needles is positioned so as to be received into the guide, and a length of each needle within the plurality of needles is 1.5 to 5.5 mm.

7. The insertion type drug injection device according to claim 1, wherein the injection member includes the drug injection port communicating with the flow path, and is formed to allow the flow path to communicate with the plurality of needles.

8. The insertion type drug injection device according to claim 1, wherein the injection member includes:
an upper body coupled to the holder unit, and including the flow path for injecting the drug, the drug injection port communicating with the flow path, and the plurality of needles communicating with the flow path; and
a lower body coupled to the upper body, and including a plurality of needle holders for the plurality of needles to be penetrated through.

9. The insertion type drug injection device according to claim 1, wherein the holder unit is formed integrally with the insert part of the main body, or detachably coupled to the insert part of the main body.

10. The insertion type drug injection device according to claim 1, wherein the main body includes an air discharge pipe coupling part, the air discharge pipe coupling part connected to the air flowing pipe inside the main body and to an air discharge pipe outside the main body.

11. The insertion type drug injection device according to claim 1, wherein each needle of the plurality of needles is positioned inward from the insert part by 0.1 to 2.5 mm.

12. The insertion type drug injection device according to claim 1, wherein the main body includes a checking means that enables checking of one or more of insertion depth and rotation angle.

13. The insertion type drug injection device according to claim 12, wherein the checking means is one or more selected from a group consisting of a scale, a partition line, numbers, symbols, letters, prints, stickers, colors, protrusions, and indication panels.

14. The insertion type drug injection device according to claim 12, wherein the checking means includes a color changing part that changes color when reacting with a liquid.

15. The insertion type drug injection device according to claim 1, wherein the main body includes a genuineness identification unit including a short-range wireless communication unit to determine a genuineness of a product by communicating with an external control unit.

16. The insertion type drug injection device according to claim 15, wherein the short-range wireless communication unit includes a NFC or RFID.

* * * * *